United States Patent
Tsukamoto et al.

(10) Patent No.: US 10,125,075 B2
(45) Date of Patent: Nov. 13, 2018

(54) P-TOLUIC ACID PRODUCTION METHOD

(71) Applicant: TORAY INDUSTRIES, INC., Tokyo (JP)

(72) Inventors: Daijiro Tsukamoto, Kamakura (JP); Satoshi Sakami, Kamakura (JP); Katsushige Yamada, Kamakura (JP); Tetsu Yonehara, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 15/552,739

(22) PCT Filed: Feb. 22, 2016

(86) PCT No.: PCT/JP2016/055122
§ 371 (c)(1),
(2) Date: Aug. 22, 2017

(87) PCT Pub. No.: WO2016/136683
PCT Pub. Date: Sep. 1, 2016

(65) Prior Publication Data
US 2018/0265445 A1    Sep. 20, 2018

(30) Foreign Application Priority Data

Feb. 23, 2015 (JP) ................. 2015-032680

(51) Int. Cl.
*C07C 51/377* (2006.01)
*C07C 63/04* (2006.01)
*C07C 51/47* (2006.01)

(52) U.S. Cl.
CPC ............ *C07C 51/377* (2013.01); *C07C 51/47* (2013.01); *C07C 63/04* (2013.01)

(58) Field of Classification Search
CPC ........ C07C 51/377; C07C 63/04; C07C 51/47
See application file for complete search history.

(56) References Cited

U.S. PATENT DOCUMENTS

| 2,712,551 A | 7/1955 | Himel et al. |
| 3,419,469 A | 12/1968 | Humphrey et al. |

FOREIGN PATENT DOCUMENTS

| DE | 2751363 A1 | | 5/1979 |
| GB | 2008114 A | | 5/1979 |
| JP | 54-79244 A | | 6/1979 |
| JP | 56-53635 A | | 5/1981 |
| JP | 9-301918 A | | 11/1997 |
| JP | 2008-534577 A | | 8/2008 |
| WO | WO 2006/103693 A1 | | 10/2006 |
| WO | WO2011/094131 | * | 8/2011 |
| WO | WO 2011/094131 A1 | | 8/2011 |
| WO | WO 2014/144843 A1 | | 9/2014 |

OTHER PUBLICATIONS

Alder et al., "Über substituierende Addition und Dien-Synthese beim Methylen-cyclobutan (IX. Mitteil. über substituierende Additionen)," Chemische Berichte, vol. 85, No. 6, 1952, pp. 556-565, with an English abstract.

Jamison et al., "Microbial Hydrocarbon Co-oxidation. III. Isolation and Characterization of an α, α'-Dimethyl-cis, cis-Muconic Acid-producing Strain of Nocardia coralline," Applied Microbiology, vol. 17, Jun. 6, 1969, pp. 853-856.

* cited by examiner

*Primary Examiner* — Jafar F Parsa
*Assistant Examiner* — Blaine G Doletski
(74) *Attorney, Agent, or Firm* — Birch, Stewart, Kolasch & Birch LLP

(57) ABSTRACT

A method for producing highly pure p-toluic acid by a simple solid-liquid separation operation using as a raw material a substance inducible from a biomass resource and suitable for fermentation production by a microorganism is disclosed.

The method for producing p-toluic acid includes: a dehydration reaction step of dehydrating Compound(s) (1)-(4), which are substances inducible from biomass resources and suitable for fermentation production by microorganisms; and a solid-liquid separation step of recovering a solid produced by this dehydration reaction by a simple solid-liquid separation operation.

2 Claims, No Drawings

P-TOLUIC ACID PRODUCTION METHOD

TECHNICAL FIELD

The present invention relates to a method for producing highly pure p-toluic acid by a simple solid-liquid separation operation using as a raw material a substance inducible from a biomass resource.

BACKGROUND ART p-Toluic acid is an important chemical product that is widely used as a raw material for producing sensitizing dyes, fluorescent dyes, anticorrosives, pigments, agricultural chemicals, and the like. The purity of standard-quality p-toluic acid is said to be 98%, and it is a chemical product generally required to have high purity. In particular, especially high purity is required for p-toluic acid for use in pharmaceuticals.

Industrial production of p-toluic acid is carried out by air oxidation of p-xylene in the presence of a cobalt salt, manganese salt, or cerium salt catalyst at 150° C. to 200° C. followed by separation and purification of p-toluic acid from the resulting crude reaction liquid (Patent Document 1).

Patent Document 2 discloses a method for producing p-toluic acid by a simple separation operation. In this method, air oxidation of p-xylene is carried out in the presence of water, and the resulting product is recovered by filtration after cooling, followed by washing with toluene. By this, a solid mainly containing p-toluic acid is obtained.

Several methods for producing highly pure p-toluic acid have been disclosed. For example, a production method in which p-xylene is removed by distillation from a p-xylene oxidation reaction crude liquid, and the resulting product is subjected to hot sulfuric acid treatment at 200° C., esterification treatment at 200° C., and then steam distillation at 230° C. has been disclosed (Patent Document 3). A production method in which p-xylene is removed by distillation from a p-xylene oxidation reaction crude liquid, and the resulting product is subjected to base treatment at 138° C. and water extraction, followed by removing the resulting salt, cooling the resulting product to allow precipitation of p-toluic acid, and then washing the p-toluic acid with hexane has been disclosed (Patent Document 4). A production method in which a p-xylene oxidation reaction crude liquid is brought into contact with an aqueous base solution and water at 120° C., and the resulting organic phase is cooled to allow precipitation of p-toluic acid, followed by washing of the p-toluic acid with p-xylene has also been disclosed (Patent Document 5).

In recent years, because of problems such as possible depletion of fossil resources in the future and global warming due to emission of greenhouse gases, methods for producing chemical products using, as raw materials, substances inducible from biomass resources, which are regenerative resources, have been demanded. As such a method, Patent Document 6 discloses a microorganism having an ability to biosynthesize p-toluic acid from glyceraldehyde-3-phosphate and pyruvic acid, and a method using the microorganism. Glyceraldehyde-3-phosphate and pyruvic acid are compounds produced by fermentation of biomass resources.

PRIOR ART DOCUMENTS

Patent Documents

[Patent Document 1] U.S. Pat. No. 2,712,551 B
[Patent Document 2] Japanese Translated PCT Patent Application Laid-open No. 2008-534577 A
[Patent Document 3] JP 56-53635 A
[Patent Document 4] JP 54-79244 A
[Patent Document 5] JP 9-301918 A
[Patent Document 6] WO 2011/094131

SUMMARY OF THE INVENTION

Problems to be Solved by the Invention

As described above, production of p-toluic acid generally includes a step of air oxidation of p-xylene. However, air oxidation of p-xylene is a reaction in which oxidation sequentially proceeds as follows: p-xylene→p-tolualdehyde→p-toluic acid→4-carboxybenzaldehyde→terephthalic acid. Therefore, normally, it is difficult to obtain the substance of interest, p-toluic acid, without contamination with other p-xylene oxidation products.

It is described, based on a result of analysis by gas chromatography, that the solid containing p-toluic acid produced by the method disclosed in Patent Document 2 contains 96.6 mol % p-toluic acid, 0.4 mol % terephthalic acid, and 3.0 mol % other oxidation products. However, the document does not describe the purity of the p-toluic acid in the solid. In view of this, the purity (by weight) of the p-toluic acid was calculated based on the assumption that the solid does not contain a product undetectable by the gas chromatography, and that all the other oxidation products are p-tolualdehyde. As a result, the purity was found to be 96.9% at most. On the other hand, it is described that 80% of the raw material p-xylene remains unreacted in this method. The method therefore has a problem that the yield is low.

Patent Documents 3 to 5 describe methods by which p-toluic acid with a purity of not less than 99% can be obtained from a p-xylene oxidation reaction crude liquid. However, in any of these methods, the purification process is a multi-step process, and requires accurate temperature control in a high-temperature range.

Thus, there is no conventional production method for p-toluic acid including a step of air oxidation of p-xylene, which method allows production of sufficiently pure p-toluic acid with a high yield by a simple purification operation. That is, for obtaining highly pure p-toluic acid, these conventional methods require large-scale facilities for the purification process, and a heavy economic burden therefor.

Patent Document 6 discloses a microorganism having an ability to biosynthesize p-toluic acid from glyceraldehyde-3-phosphate and pyruvic acid through the later-mentioned Compound (1), and a method which is said to be capable of producing p-toluic acid using the microorganism. However, since there is no description of an example of production of p-toluic acid by this method, whether p-toluic acid can be actually produced or not is unclear. In general, in production of a substance using a microorganism, it is preferred to maintain the oxidation-reduction balance determined by the ratio between NADH and NAD+ in the cell. However, Patent Document 6 describes that production of p-toluic acid by this method causes accumulation of NAD+, and it is therefore thought that the oxidation-reduction balance is not maintained in this method. Thus, production of p-toluic acid by this method is assumed to be difficult.

In view of the current situation described above, a method for producing highly pure p-toluic acid by a simple purification operation using as a raw material a substance inducible from a biomass resource and suitable for fermentation production by a microorganism is demanded.

Means for Solving the Problems

As a result of intensive study to solve the problems described above, the present inventors discovered that highly pure p-toluic acid can be produced by simple solid-liquid separation using as a raw material one or more compounds selected from Compound (1), Compound (2), Compound (3), and Compound (4), which are substances inducible from biomass resources, thereby completing the present invention.

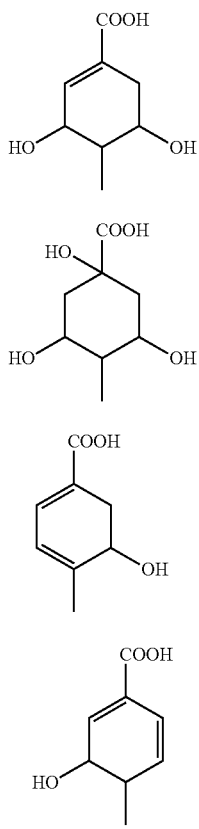

Compound (1)

Compound (2)

Compound (3)

Compound (4)

That is, the present invention provides a method for producing p-toluic acid, the method comprising: a dehydration reaction step of performing dehydration reaction of one or more compounds selected from the Compound (1) to Compound (4) shown in Scheme 1; and a step of performing solid-liquid separation of a solid produced by the dehydration reaction step.

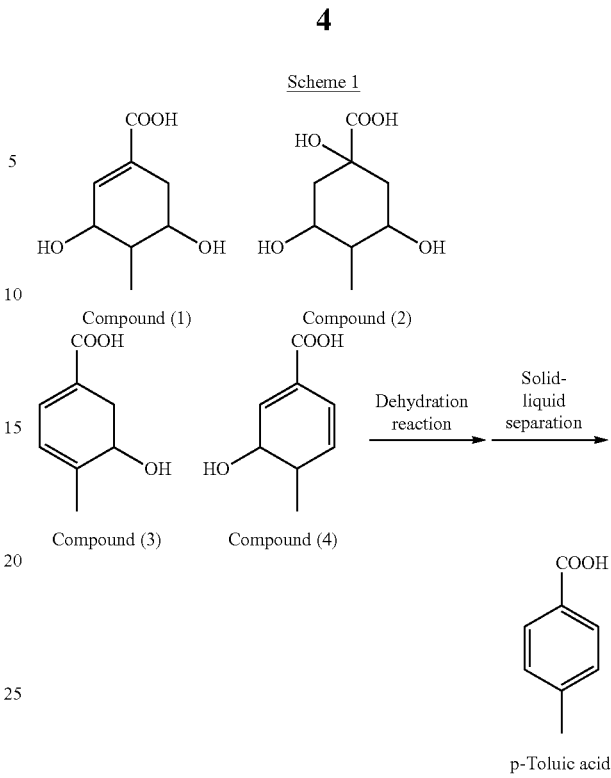

Scheme 1

Compound (1)  Compound (2)

Compound (3)  Compound (4)

Dehydration reaction → Solid-liquid separation → p-Toluic acid

In one embodiment of the present invention, the dehydration reaction step is a step of allowing an acid to act on the compound(s) in an aqueous solution.

Effect of the Invention

The present invention enables production of highly pure p-toluic acid by simple solid-liquid separation using as a raw material Compound(s) (1)-(4), which are substances inducible from biomass resources and suitable for fermentation production by microorganisms.

MODE FOR CARRYING OUT THE INVENTION

In the present invention, a biomass resource means a regenerative organic resource derived from an organism(s), and means a resource composed of an organic matter produced by carbon dioxide fixation using solar energy by a plant(s). Specific examples of the biomass resource include coffee beans, cinchona bark, sugar beet, tara beans, tobacco leaves, pear leaves, tea leaves, apple, cranberry, hawthorn, sugarcane, maize, tubers, wheat, rice, soybean, pulp, kenaf, rice straw, wheat straw, bagasse, corn stover, switchgrass, weeds, waste paper, woods, charcoal, natural rubber, cotton, soybean oil, palm oil, safflower oil, and castor oil.

In the present invention, a substance inducible from a biomass resource means a substance that is induced, that can be induced, or that was induced from the biomass resource by biological conversion, chemical conversion, or the like.

In the present invention, the Compound(s) (1)-(4) to be used as a raw material for p-toluic acid can be induced from a biomass resource(s). For example, Compound (1) and Compound (2) can be induced from quinic acid (Compound (5)) as shown in Scheme 2. Quinic acid can be produced by biological conversion (disclosed in, for example, JP 2009-201473 A) or chemical conversion (disclosed in, for example, JP 7-8169 A) using as a raw material coffee beans, cinchona bark, sugar beet, or the like. More specifically, JP 2009-201473 A discloses a method for producing quinic acid from chlorogenic acid contained in coffee grounds using as a microbial catalyst coffee-ground koji prepared from a filamentous fungus such as *Aspergillus niger*. JP 7-8169 A discloses a method for extraction and purification of quinic acid by subjecting raw coffee beans and/or a coffee extraction residue to alkaline hydrolysis, strongly basic anion exchange resin treatment, strongly acidic cation exchange resin treatment, and ion-exchange membrane electrodialysis treatment. Quinic acid can also be produced by fermentation of glucose (U.S. Pat. No. 6,600,077 B), and glucose can be produced from cellulose, which is a major component of biomass, by a conventional method.

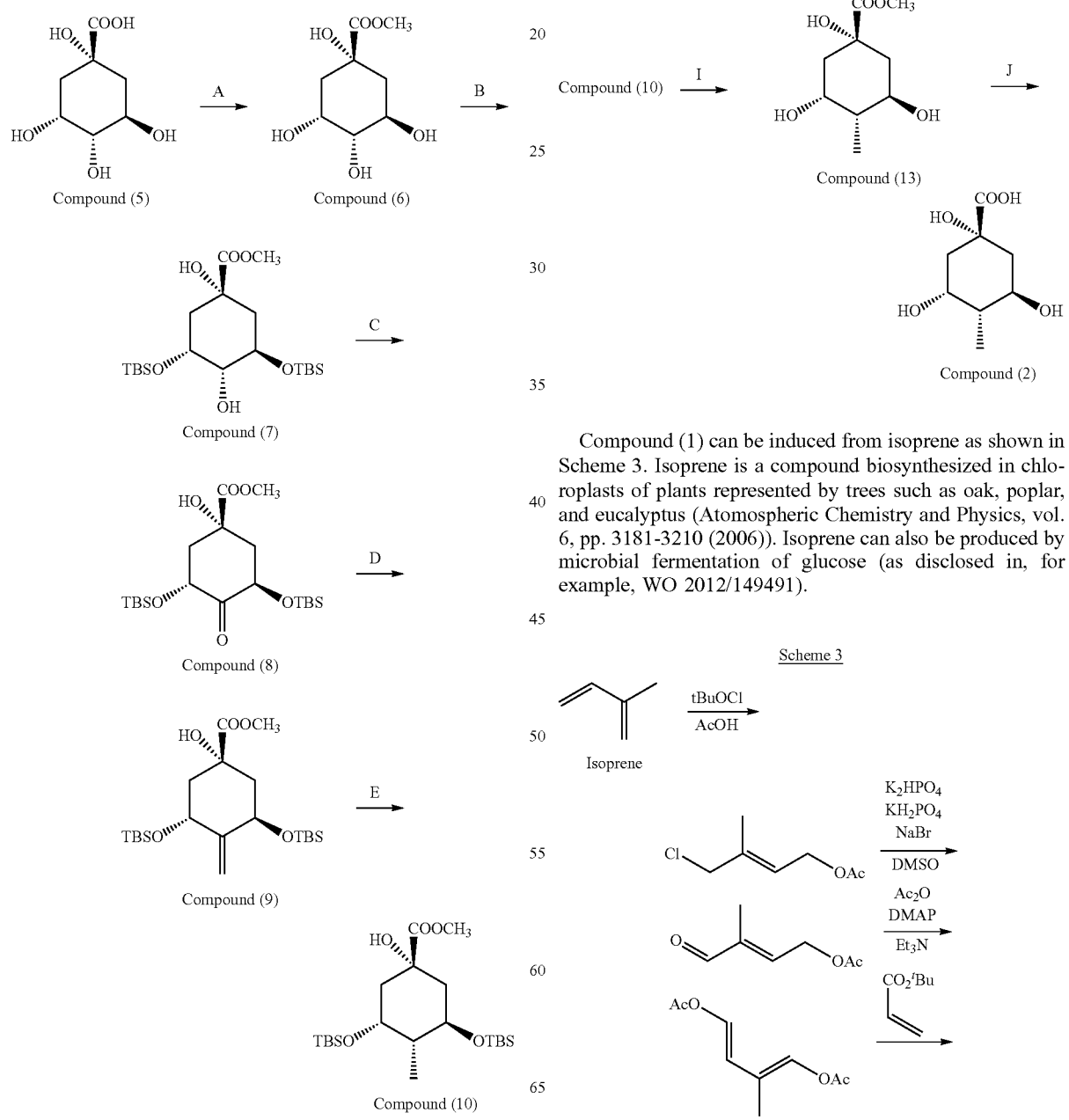

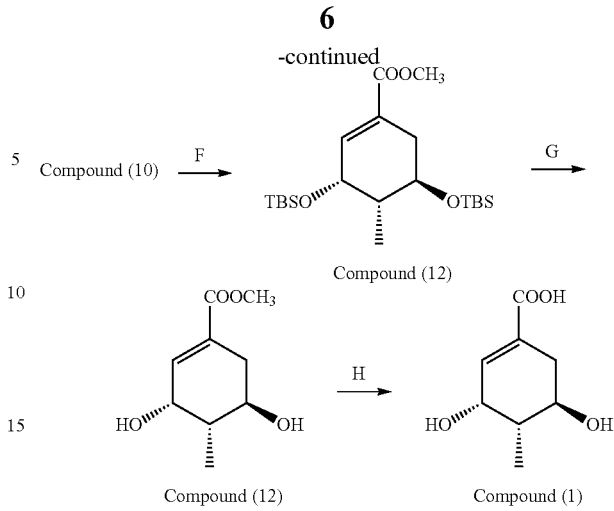

Compound (1) can be induced from isoprene as shown in Scheme 3. Isoprene is a compound biosynthesized in chloroplasts of plants represented by trees such as oak, poplar, and eucalyptus (Atmospheric Chemistry and Physics, vol. 6, pp. 3181-3210 (2006)). Isoprene can also be produced by microbial fermentation of glucose (as disclosed in, for example, WO 2012/149491).

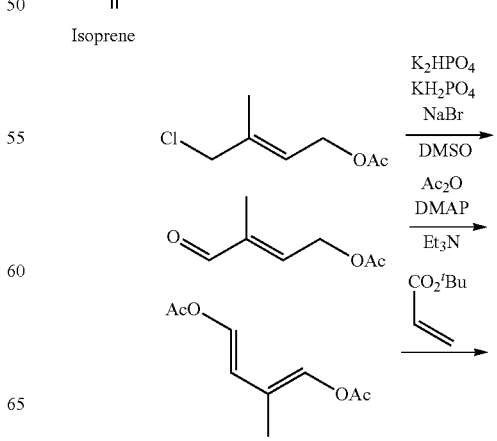

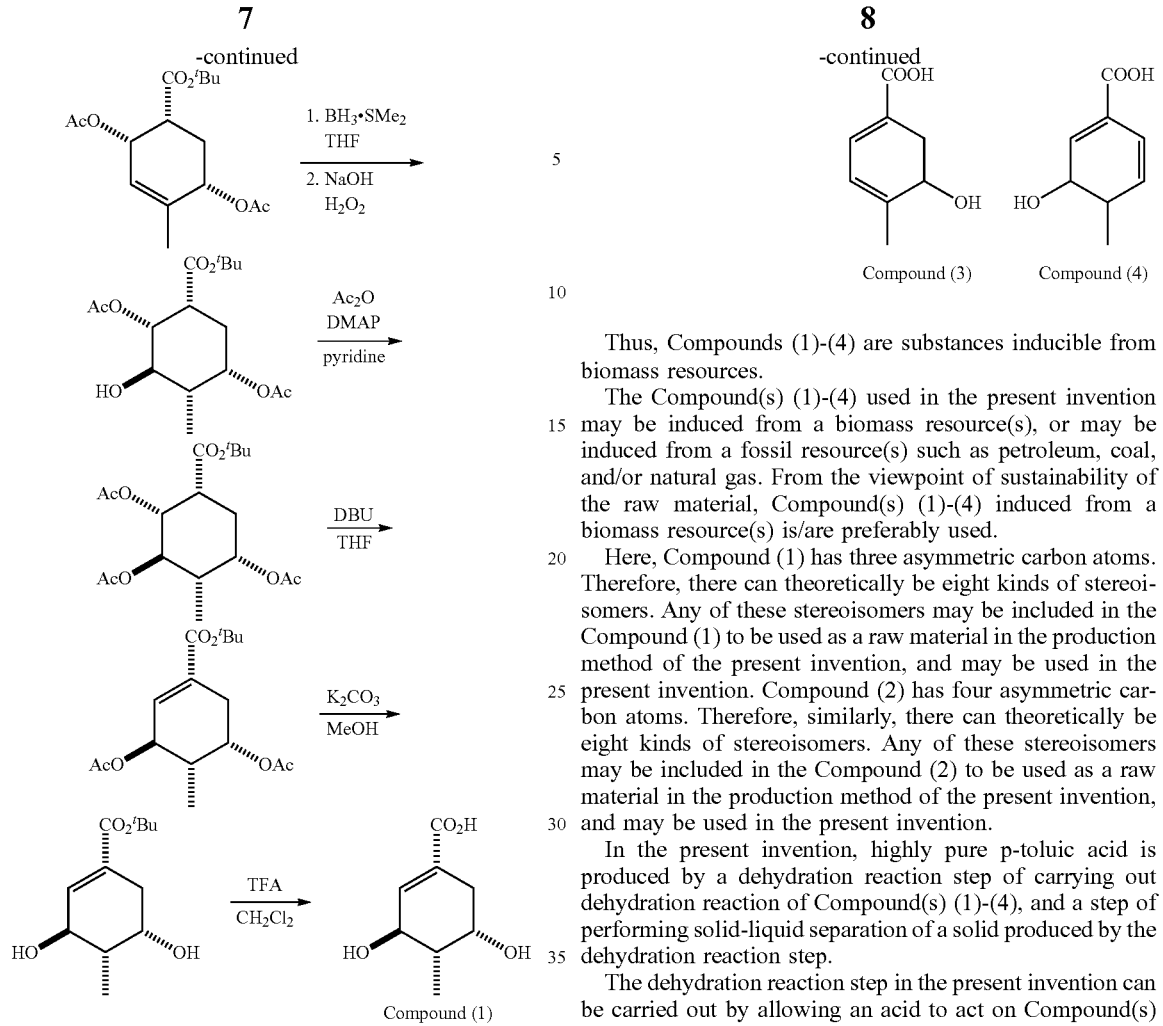

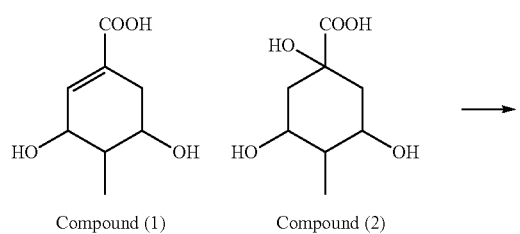

Compounds (3) and (4) can be produced by biological or chemical dehydration of Compound (1) or (2) as shown in Scheme 4. Examples of enzymes that can convert Compound (1) or (2) to Compound (3) or (4) include 3-dehydroquinate dehydratase (EC 4.2.1.10), 4α-carbinolamine dehydratase (EC 4.2.1.96), 5α-hydroxysterol dehydratase (EC 4.2.1.62), myo-inosose-2 dehydratase (EC 4.2.1.44), prephenate dehydratase (EC 4.2.1.51), and scytalone dehydratase (EC 4.2.1.94). Compounds (3) and (4) can also be synthesized by allowing an acid such as hydrochloric acid, sulfuric acid, hydrofluoric acid, hydrobromic acid, hydroiodic acid, nitric acid, formic acid, phosphoric acid, p-toluenesulfonic acid, methanesulfonic acid, zeolite, silica-alumina, alumina, zirconia sulfide, heteropoly acid, or ion-exchange resin to gently act on Compound (1) and/or (2).

Thus, Compounds (1)-(4) are substances inducible from biomass resources.

The Compound(s) (1)-(4) used in the present invention may be induced from a biomass resource(s), or may be induced from a fossil resource(s) such as petroleum, coal, and/or natural gas. From the viewpoint of sustainability of the raw material, Compound(s) (1)-(4) induced from a biomass resource(s) is/are preferably used.

Here, Compound (1) has three asymmetric carbon atoms. Therefore, there can theoretically be eight kinds of stereoisomers. Any of these stereoisomers may be included in the Compound (1) to be used as a raw material in the production method of the present invention, and may be used in the present invention. Compound (2) has four asymmetric carbon atoms. Therefore, similarly, there can theoretically be eight kinds of stereoisomers. Any of these stereoisomers may be included in the Compound (2) to be used as a raw material in the production method of the present invention, and may be used in the present invention.

In the present invention, highly pure p-toluic acid is produced by a dehydration reaction step of carrying out dehydration reaction of Compound(s) (1)-(4), and a step of performing solid-liquid separation of a solid produced by the dehydration reaction step.

The dehydration reaction step in the present invention can be carried out by allowing an acid to act on Compound(s) (1)-(4). The acid to be allowed to act in the dehydration reaction step is not limited as long as it allows intramolecular dehydration reaction of Compound(s) (1)-(4) to proceed. Examples of the acid include homogeneous acid catalysts such as hydrochloric acid, sulfuric acid, hydrofluoric acid, hydrobromic acid, hydroiodic acid, nitric acid, formic acid, phosphoric acid, p-toluenesulfonic acid, and methanesulfonic acid; and heterogeneous acid catalysts such as zeolite, silica-alumina, alumina, zirconia sulfide, heteropoly acid, and ion-exchange resins.

The Compound(s) (1)-(4) used in the dehydration reaction step of the present invention may be either in the form of a salt, or a mixture of a free form and a salt. The salt may be any of lithium salt, sodium salt, potassium salt, rubidium salt, cesium salt, ammonium salt, magnesium salt, calcium salt, and the like, or may be a mixture of any of these.

In the dehydration reaction step of the present invention, any one compound selected from Compounds (1) to (4) may be used alone, or a mixture of two or more compounds selected from Compounds (1) to (4) may be used, as a raw material.

The solvent used in the dehydration reaction step in the present invention is not limited as long as it does not affect the reaction. Examples of solvents that may be used therefor include water; hydrocarbons such as hexane; acetic acid esters such as ethyl acetate; ketones such as acetone; ethers such as diethyl ether; and halogenated hydrocarbons such as dichloromethane. Among these, solvents in which Compound(s) (1)-(4) as the raw material is/are highly soluble, and in which p-toluic acid as the product is poorly soluble, are preferred. In cases where the solubility of Compound(s) (1)-(4) is high, control of the reaction temperature can be easily carried out, and the amount (concentration) of the raw material to be fed can be increased, for the purpose of increasing the reaction rate. On the other hand, in cases where the solubility of p-toluic acid as the product is low, p-toluic acid can be easily allowed to precipitate as a solid (crystals) in the reaction system. In such cases, the reaction rate can be increased, and p-toluic acid as the product can be separated (isolated) by a simple solid-liquid separation operation.

Specific examples of such solvents include water. A study by the present inventors revealed that the solubilities of Compounds (1) and (2) in water are as high as not less than 50 g/L at pH 7 at 25° C. On the other hand, the solubility of p-toluic acid in water is known to be 0.3 g/L at pH 7 at 25° C., and a study by the present inventors revealed that the solubility is not more than 0.1 g/L at pH 0 at 25° C. Accordingly, in the dehydration reaction step, especially in cases where Compound (1) or (2) is used as a raw material, use of water as the solvent is preferred from an economic and environmental point of view.

The reaction temperature in the dehydration reaction step in the present invention is not limited. In cases where water is used as the solvent, the reaction temperature is preferably from 80° C. to 140° C., more preferably from 90° C. to 120° C., still more preferably from 95° C. to 110° C.

The pressure in the dehydration reaction step in the present invention is not limited. In cases where water is used as the solvent, the pressure is preferably from 0.1 atm to 10 atm, more preferably from 0.5 atm to 3 atm. In particular, the step is preferably simply carried out under atmospheric pressure, wherein no apparatus or operation for pressure reduction or pressurization is required.

The atmosphere in the dehydration reaction step in the present invention is not limited, and any of air, oxygen, nitrogen, helium, argon, hydrogen, water vapor, and mixed gases thereof may be used. Air is preferably used from the viewpoint of simplicity.

In the present invention, the p-toluic acid produced as a solid (crystals) in the reaction system as a result of the dehydration reaction step can be recovered by separation from the reaction crude liquid by a solid-liquid separation step.

The method of the solid-liquid separation in the solid-liquid separation step in the present invention is not limited, and a common solid-liquid separation operation may be employed. For example, filtration separation, centrifugation, sedimentation, membrane separation, or the like may be used, and any combination of these methods may also be used.

The temperature in the solid-liquid separation step in the present invention is not limited, and preferably from −10° C. to 70° C., more preferably from 0° C. to 50° C. By using a temperature lower than the reaction temperature in the dehydration reaction step, precipitation of p-toluic acid can be promoted. In particular, the step is preferably simply carried out at normal temperature, wherein no apparatus or operation for heating or cooling is required.

The atmosphere in the solid-liquid separation step in the present invention is not limited, and any of air, oxygen, nitrogen, helium, argon, hydrogen, water vapor, and mixed gases thereof may be used. Air is preferably used from the viewpoint of simplicity.

The p-toluic acid after the solid-liquid separation may be washed with an appropriate solvent. Examples of solvents that may be used for the washing of p-toluic acid include water, methanol, ethanol, isopropanol, hexane, benzene, toluene, xylene, diethyl ether, tetrahydrofuran, 1,4-dioxane, ethyl acetate, chloroform, and dichloromethane. Water is preferably used. Since solubility of p-toluic acid in water is not high, the amount of highly pure p-toluic acid recovered can be increased by washing with water.

The mother liquor containing p-toluic acid produced in the solid-liquid separation step may be recycled to be used for the dehydration reaction step and/or solid-liquid separation step. By the recycling, the amounts of the acid and the solvent to be used can be reduced, and the recovery of the p-toluic acid can be increased. The method of the recycling of the mother liquor is not limited, and examples of the method include recycling of the whole amount of the mother liquor, and recycling after concentration of the mother liquor.

The present invention is characterized in that highly pure p-toluic acid can be obtained by a simple solid-liquid separation step. The solid-liquid separation step may be used in combination with a conventionally known separation operation(s) such as gas absorption, adsorption/ion exchange, extraction, distillation, crystallization, and/or the like.

EXAMPLES

The present invention is described below in more detail by way of Examples. However, the present invention is not limited to the Examples below.

Reference Example 1 Synthesis of Compound (1) and Compound (2)

Compound (1) and Compound (2) were synthesized according to the pathway shown in Scheme 2 as described in the following (A) to (J).

(A) Synthesis of Compound (6): Methyl (1S,3R,4S,5R)-1,3,4,5-tetrahydroxycyclohexanecarboxylate Quinic acid (manufactured by Tokyo Chemical Industry Co., Ltd.; 5 g; 26 mmol) (Compound (5)) was dissolved in methanol (manufactured by Kokusan Chemical Co., Ltd.; 40 mL), and 10% hydrochloric acid solution in methanol (manufactured by Tokyo Chemical Industry Co., Ltd.; 10 mL) was added to the resulting solution, followed by stirring the resulting mixture at 40° C. for 9.5 hours. After concentrating the mixture with a rotary evaporator (manufactured by Tokyo Rikakikai Co., Ltd.), toluene (manufactured by Wako Pure Chemical Industries, Ltd.; 100 mL) was added to the mixture, and the resulting mixture was concentrated with a rotary evaporator, followed by drying under reduced pressure. The resulting crudely purified product of Compound (6) was used as it is for the subsequent reaction (yield, 6.54 g).

(B) Synthesis of Compound (7): Methyl (1S,3R,4S,5R)-3,5-bis(tert-butyldimethylsilyloxy)-1,4-dihydroxycyclohexanecarboxylate The crudely purified product of Compound (6) (6.54 g) was dissolved in dimethylformamide (manufactured by Wako Pure Chemical Industries, Ltd.; 50 mL), and tert-butyldimethylchlorosilane (manufactured by Tokyo Chemical Industry Co., Ltd.; 4.75 g, 31.5 mmol) and triethylamine (manufactured by Wako Pure Chemical Industries, Ltd.; 5.47 mL, 39.5 mmol) were added to the resulting solution, followed by stirring the resulting mixture at room temperature for 17.5 hours, further adding tert-butyldimethylchlorosilane (4.75 g, 31.5 mmol) and triethylamine (5.47 mL, 39.5 mmol) thereto, and then stirring the resulting mixture at 40° C. for 3 hours. Distilled water (150 mL) and ether (250 mL) were added to the mixture, followed by separation. The organic layer was washed with distilled water and saturated brine, and then concentrated (9.42 g) by drying over anhydrous sodium sulfate (manufactured by Wako Pure Chemical Industries, Ltd.). The resulting crudely purified product was purified by silica gel column chromatography (medium pressure; silica gel, 100 g; hexane (manufactured by Kokusan Chemical Co., Ltd.): ethyl acetate (manufactured by Wako Pure Chemical Industries, Ltd.)=80:20–30:70) to obtain Compound (7) (1.70 g; two-step, 15%) and a compound in which one tert-butyldimethylsilyloxy group is introduced in Compound (6) (1.86 g, two-step, 22%).

A tert-butyldimethylsilyloxy group was introduced to the compound in which one tert-butyldimethylsilyloxy group is introduced in Compound (6) (1.86 g), by the same procedure as described above, to obtain Compound (7) (2.14 g, 85%).

(C) Synthesis of Compound (8): Methyl (3R,5R)-3,5-bis(tert-butyldimethylsilyloxy)-1-hydroxy-4-oxocyclohexanecarboxylate Compound (7) (10.63 g, 24.5 mmol) was dissolved in a mixture of methylene chloride (manufactured by Wako Pure Chemical Industries, Ltd.; 60 mL) and saturated sodium bicarbonate water (60 mL), and potassium bromide (manufactured by Wako Pure Chemical Industries, Ltd.; 0.292 g, 2.45 mmol) and 2-hydroxy-2-azaadamantane (manufactured by Tokyo Chemical Industry Co., Ltd.; 37.5 mg; 0.245 mmol) were added to the resulting solution, followed by stirring the resulting mixture at room temperature. Sodium chlorate (manufactured by Wako Pure Chemical Industries, Ltd.; 6.05 g; 36.8 mmol) was slowly added to the mixture, and the resulting mixture was stirred for 2 hours. To the resulting mixture, 0.1 mol/L aqueous sodium thiosulfate solution (6 mL) was added, and the mixture was then stirred for 30 minutes, followed by adding the resulting reaction liquid to distilled water and performing extraction with methylene chloride. By collecting the organic layer and concentrating the collected organic layer by drying over anhydrous magnesium sulfate (manufactured by Wako Pure Chemical Industries, Ltd.), Compound (8) was obtained (10.49 g, 99%).

(D) Synthesis of Compound (9): Methyl (3R,5R)-3,5-bis(tert-butyldimethylsilyloxy)-1-hydroxy-4-methylenecyclohexanecarboxylate Methyltriphenylphosphonium bromide (manufactured by Tokyo Chemical Industry Co., Ltd.; 2.36 g) was dissolved in tetrahydrofuran (manufactured by Wako Pure Chemical Industries, Ltd.; 25 mL), and n-butyllithium (2.65 mol/L, solution in n-hexane, 2.31 mL) was added to the resulting solution at 0° C., followed by stirring the resulting mixture at room temperature for 30 minutes. The mixture was then cooled to −14° C. (in an ethanol/ice bath), and a solution of Compound (8) (1.06 g, 2.45 mmol) in tetrahydrofuran (15 mL) was added dropwise thereto, followed by stirring the resulting mixture at room temperature for 3.5 hours. The reaction liquid was added to a mixture of distilled water and saturated brine at 0° C., and extraction with ethyl acetate was carried out. The organic layer was collected, and concentrated by drying over anhydrous sodium sulfate. By purification by silica gel column chromatography (medium pressure, hexane/ethyl acetate=97/3–85/15), Compound (9) (257 mg, 24%) was obtained.

(E) Synthesis of Compound (10): Methyl (1S,3R,4S,5R)-3,5-bis(tert-butyldimethylsilyloxy)-1-hydroxy-4-methylcyclohexanecarboxylate Compound (9) (257 mg, 0.597 mmol) was dissolved in methanol (10 mL), and 10% palladium/activated carbon (manufactured by Sigma-Aldrich, 70 mg) was added to the resulting solution, followed by stirring the resulting mixture in a hydrogen atmosphere at room temperature for 15 hours. The reaction liquid was filtered, and the resulting filtrate was concentrated. By purification by silica gel column chromatography (medium pressure, hexane/ethyl acetate=95/5–90/10), Compound 10 (89 mg, 34%) was obtained. The stereochemistry of Compound (10) was confirmed by analysis using an X-ray crystal structure analyzer (manufactured by Rigaku Corporation).

(F) Synthesis of Compound (11): Methyl (3R,4S,5R)-3,5-bis(tert-butyldimethylsilyloxy)-4-methyl-1-cyclohexenecarboxylate Compound (10) (236 mg, 0.545 mmol) was dissolved in methylene chloride (5 mL), and a solution of bis[α,α-bis(trifluoromethyl)benzenemethanolato]diphenylsulfur (manufactured by Tokyo Chemical Industry Co., Ltd.; 513 mg, 0.763 mmol) in methylene chloride (2 mL) was added to the resulting solution, followed by stirring the resulting mixture at room temperature for 17 hours. After purification of the reaction liquid by silica gel column chromatography (medium pressure, hexane/ethyl acetate=100/0–92/8), repurification by silica gel column chromatography (medium pressure, hexane/ethyl acetate=100/0–92/8) was carried out to obtain Compound (11) (208 mg, 92%).

(G) Synthesis of Compound (12): Methyl (3R,4S,5R)-3,5-dihydroxy-4-methyl-1-cyclohexenecarboxylate Compound (11) (1.00 g, 2.41 mmol) was dissolved in methanol (18 mL), and 10% hydrogen chloride solution in methanol (2 mL) was added to the resulting solution, followed by stirring the resulting mixture at room temperature for 2.5 hours. The reaction liquid was concentrated to obtain a crudely purified product of Compound (12) (566 mg).

(H) Synthesis of Compound (1)

The crudely purified product of Compound (12) (566 mg) was dissolved in methanol (20 mL), and 1 mol/L aqueous sodium hydroxide solution (manufactured by Nacalai Tesque, Inc.; 4.8 mL) was added to the resulting solution, followed by stirring the resulting mixture at room temperature for 13 hours. The mixture was then cooled to 0° C., and 1 mol/L hydrochloric acid (manufactured by Nacalai Tesque, Inc.; 4.8 mL) was added thereto (pH 3 to 4), followed by concentrating the resulting mixture. The obtained mixture was purified by HPLC (manufactured by Agilent Technologies) to obtain Compound (1) (356 mg; two-step, 76%).

Compound (1):$^1$H-NMR (400 MHz, $CD_3OD$) δ: 0.97-1.01 (3H, d), 1.81-1.87 (1H, m), 2.07-2.14 (1H, m), 2.60-2.67 (1H, m), 3.77-3.82 (1H, m), 4.37 (1H, s), 6.83-6.85 (1H, m). ESI-MS: m/z=171 $(M-H)^-$ (I) Synthesis of Compound (13): Methyl (1S,3R,4S,5R)-1,3,5-trihydroxy-4-methylcyclohexanecarboxylate Compound (10) (0.25 g, 2.41 mmol) was dissolved in methanol (10 mL), and 10% hydrogen chloride solution in methanol (1 mL) was added to the resulting solution, followed by stirring the resulting mixture at room temperature for 3.5 hours. The reaction liquid was concentrated to obtain a crudely purified product of Compound (13) (130mg).

(J) Synthesis of Compound (2)

The crudely purified product of Compound (13) (130 mg) was dissolved in methanol (6 mL), and 1 mol/L aqueous sodium hydroxide solution (0.6 mL) was added to the resulting solution, followed by stirring the resulting mixture at room temperature for 17 hours. The mixture was then cooled to 0° C., and 1 mol/L hydrochloric acid (0.6 mL) was added thereto, followed by concentrating the resulting mixture. The obtained mixture was purified by HPLC to obtain white crystals of Compound (2) (74 mg; two-step, 61%).

Compound (2): $^1$H-NMR (400 MHz, CD$_3$OD) δ: 1.14-1.15 (3H, d), 1.45-1.54(1H, m), 1.75-1.81 (1H, m), 1.98-2.00 (2H, m), 2.11-2.15 (1H, m), 3.74-3.82 (1H, m), 3.94-3.97 (1H, m). ESI-MS: m/z=189 (M−H)$^−$

[Purity/Yield of p-Toluic Acid]

The purity of the p-toluic acid shown in the following Example 1 was investigated by dissolving 10 mg of white crystals recovered by solid-liquid separation in 10 mL of water/acetonitrile (1:1), and analyzing the resulting solution by high-performance liquid chromatography (HPLC). The purity (%) of the p-toluic acid was calculated according to the following formula (Equation 1).

Purity of p-toluic acid (%)=(weight of p-toluic acid) (g)/(weight of white crystals)(g)×100  (Equation 1)

The yield of p-toluic acid shown in each of the following Examples 2 to 5 was investigated by neutralizing the reaction solution after the dehydration reaction step, adding water/acetonitrile (1:1) thereto to prepare a total of 10 mL of a solution, and then analyzing the solution by HPLC. The yield (%) of the p-toluic acid was calculated according to the following formula (Equation 2).

Yield of p-toluic acid (%)=(amount of p-toluic acid/amount of raw material)×100  (Equation 2)

The p-toluic acid concentration in the solution in the measurement was analyzed by an external standard method using a standard solution prepared from p-toluic acid (manufactured by Oakwood Products, Inc.; purity, not less than 99%). The HPLC analysis conditions were as follows.

Column: ZORBAX SB-Aq, manufactured by Agilent Technologies

Column temperature: 40° C.

Mobile phase: 0.1% aqueous phosphate solution:acetonitrile (95:5)

Mobile phase flow rate: 1 mL/min.

Detector: photodiode array (detection wavelength, 210 nm)

Example 1

In a 300-mL eggplant flask, Compound (1) (1.0 g) and 35% hydrochloric acid (100 mL) were placed, and the mixture was stirred at 95° C. for 3 hours, followed by cooling to 0° C. The precipitated solid was separated by filtration, and washed with cold water (10 mL), followed by drying under reduced pressure to obtain p-toluic acid as white crystals (0.62 g). The yield of the p-toluic acid was 78%, and the purity of the p-toluic acid was not less than 99% (HPLC).

Example 2

In a 10-mL test tube, Compound (1) (10mg) and 35% hydrochloric acid (1 mL) were placed, and the mixture was stirred at 95° C. for 7 hours, followed by cooling to 0° C. As a result, white crystals were precipitated. The precipitated crystals were separated in the same manner as in Example 1, to obtain p-toluic acid. The yield of the p-toluic acid was 97% (HPLC).

Example 3

An experiment was carried out in the same manner as in Example 2 except that 18% hydrochloric acid was used instead of 35% hydrochloric acid. As a result, p-toluic acid was obtained as white crystals. The yield of the p-toluic acid was 96% (HPLC). clp Example 4

An experiment was carried out in the same manner as in Example 2 except that 30% sulfuric acid was used instead of 35% hydrochloric acid. As a result, p-toluic acid was obtained as white crystals. The yield of the p-toluic acid was 27% (HPLC).

Example 5

In a compact autoclave container (manufactured by Taiatsu Techno), Compound (2) (10mg) and 35% hydrochloric acid (1.5 mL) were placed, and the container was sealed, followed by stirring the mixture at 130° C. for 2 hours and then cooling the mixture to 0° C. As a result, crystals were precipitated. The precipitated crystals were separated in the same manner as in Example 1, to obtain p-toluic acid. The yield of the p-toluic acid was 54%.

As shown in Example 1, p-toluic acid having a purity of not less than 99.0% (by weight) could be produced by allowing Compound (1) to act with an acid in an aqueous solution to perform dehydration reaction, and then recovering the produced solid (crystals) by simple solid-liquid separation. This purity was higher than the purity (which can be calculated as 96.9% at most) of p-toluic acid produced by the method disclosed in Patent Document 2.

It was also shown, as shown in Examples 2 to 5, that p-toluic acid can be obtained with high yield by allowing Compound (1) or Compound (2) to act with an acid in an aqueous solution. It was also shown that precipitation of p-toluic acid as a solid (crystals) occurs after the reaction.

The above Examples 1 to 5 showed examples of production of p-toluic acid using Compound (1) or (2) as a raw material. p-Toluic acid can be similarly produced in cases where Compound (3) or Compound (4), instead, is used as a raw material.

INDUSTRIAL APPLICABILITY

The present invention enables production of highly pure p-toluic acid by a simple solid-liquid separation operation using as a raw material a substance inducible from a biomass resource and suitable for feiiiientation production by a microorganism. By the present invention, raw materials for chemical products produced from p-toluic acid, such as sensitizing dyes, fluorescent dyes, anticorrosives, pigments, agricultural chemicals, and pharmaceuticals, can be switched from fossil resources to biomass resources. Thus, since the present invention can contribute to switching to a sustainable, recycling-oriented society, the present invention is industrially very useful.

The invention claimed is:

1. A method for producing p-toluic acid, said method comprising:
   a dehydration reaction step of performing dehydration reaction of one or more compounds selected from the group consisting of the following Compound (1), Compound (2), Compound (3), and Compound (4); and a step of recovering a solid produced by the dehydration reaction step by solid-liquid separation
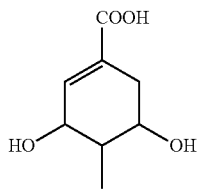
Compound (1)
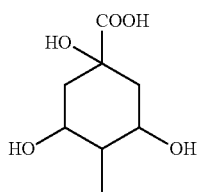
Compound (2)
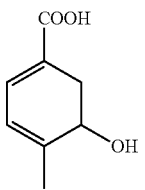
Compound (3)
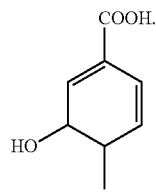
Compound (4)
2. The production method according to claim 1, wherein said dehydration reaction step comprises allowing an acid to act on said compound(s) in an aqueous solution.
* * * * *